United States Patent
Kirchgeorg

[11] Patent Number: 5,813,423
[45] Date of Patent: Sep. 29, 1998

[54] INHALATOR AND/OR RESUSCITATOR MASK ADAPTABLE FOR USE WITH AN ADULT AND CHILD

[76] Inventor: John Kirchgeorg, 1776 N. Water St. P.O. Box 3000, Milwaukee, Wis. 53201

[21] Appl. No.: 736,589

[22] Filed: Oct. 24, 1996

Related U.S. Application Data

[63] Continuation of Ser. No. 551,612, Nov. 1, 1995, abandoned.

[51] Int. Cl.⁶ .................................................. A61M 16/00
[52] U.S. Cl. ................................ 128/202.28; 128/205.25
[58] Field of Search ........................ 128/202.28, 205.25, 128/206.24, 206.26; 2/9, 206, 244, 246

[56] References Cited

U.S. PATENT DOCUMENTS

| | | | |
|---|---|---|---|
| 1,653,572 | 12/1927 | Jackson | 128/206.24 |
| 2,254,854 | 9/1941 | O'Connell | 128/206.26 |
| 2,280,050 | 4/1942 | Alexander et al. | 128/203.11 |
| 2,441,333 | 5/1948 | Reinsberg | 2/206 |
| 2,877,764 | 3/1959 | Galleher, Jr. | 128/206.24 |
| 2,964,757 | 12/1960 | Jarvis | 2/206 |
| 2,990,838 | 7/1961 | Cross | |
| 3,206,760 | 9/1965 | Santala | 2/9 |
| 3,357,426 | 12/1967 | Cohen | |
| 4,151,843 | 5/1979 | Brekke et al. | |
| 4,226,234 | 10/1980 | Gunderson | 128/205.25 |
| 5,088,485 | 2/1992 | Schock | 128/202.28 |
| 5,121,745 | 6/1992 | Isreal | 128/202.28 |
| 5,295,478 | 3/1994 | Baldwin | 128/202.28 |
| 5,429,683 | 7/1995 | Le Mitouard | 128/206.26 |
| 5,469,842 | 11/1995 | Flynn | 128/202.28 |

*Primary Examiner*—Aaron J. Lewis
*Attorney, Agent, or Firm*—Sughrue, Mion, Zinn, Macpeak & Seas, PLLC

[57] ABSTRACT

An inhalator and/or resuscitator mask that is capable for use with both a child and an adult. Specifically, the mask has indicia printed on its face to indicate which way it is to be positioned when used on either an adult or a child. The indicia axis of orientation indicates one axis of orientation of the mask when the mask is applied to an adult, and indicates the other axis of orientation of the mask when the mask is applied to a child.

12 Claims, 5 Drawing Sheets

INHALATOR AND/OR RESUSCITATOR MASK ADAPTABLE FOR USE WITH AN ADULT AND CHILD

This is a continuation of application Ser. No. 08/551,612 filed Nov. 1, 1995 now abandoned.

BACKGROUND OF THE INVENTION

1. Field of the Invention

The present invention relates to an inhalator and/or resuscitator mask adaptable for use on both adult and child patients simply by positioning the mask in a certain manner as directed by indicia disposed on the surface of the mask.

2. Description of the Related Art

Inhalator and/or resuscitator masks which are used to provide emergency oxygen and/or resuscitation to a victim at an accident scene or in a hospital emergency room have been known in the medical field for many years. These masks are typically soft and made from a durable flexible material such as rubber, plastic, or the like.

These masks sometimes have straps which are capable of securing the mask to the face of the victim or patient. As shown in FIG. 1, a conventional mask 1 has a wide end 3 and a narrow end 5, and straps 7 attached to its sides. The mask sometimes includes a hole 11 into which a tube (not shown) is inserted to provide oxygen to the mask 1. The mask sometimes includes a hole (2) to which is applied positive pressure to resuscitate the victim, or holes, which allow inhalation and exhalation as free breathing masks.

When positioning the mask on a patient or victim, the wide end 3 of the mask 1 is placed proximate to the chin of the patient while the narrow end 5 of the mask 1 is placed on the bridge of the patient's nose as shown, for example, in FIG. 2. These conventional masks are designed to produce a substantially air tight seal between the mask and the victim's face when the victim's face is of an adult size.

However, as shown, for example, in FIG. 3, when these masks are used on a child, the mask cannot fit properly on the child's face and therefore, much space is present between the mask and the child's face, thus preventing a tight-seal fit. To remedy this, smaller child-size masks have been available. Hence, when attempting to administer oxygen and/or resuscitation to a child, a rescuer providing medical aid must select this smaller size mask.

However, in an emergency situation, if the larger adult mask is already attached to the oxygen supply and/or one-way valve and/or resuscitator bag, the rescuer must quickly locate a child-sized mask and replace the standard mask with the child-size mask in order to supply oxygen and/or resuscitation effectively to the child. At the very least, the rescuer must make a conscious effort to select the child-size mask as opposed to a standard adult-size mask. This wastes valuable time which could adversely affect the child's chances of survival. Also, because extra space is necessary to store these additional child-size masks and to identify them as such, the overall medical equipment storage space is increased. It has also been known that in some cases a conventional mask can be placed on a child's face in an "upside-down" fashion and can obtain an effective seal. However, this knowledge is not widespread and no attempt has previously been made to design a mask which capitalizes on this possibility and which contains any indication of this dual-use capability.

SUMMARY OF THE INVENTION

To remedy the problems discussed above, the present invention provides an inhalator and/or resuscitator mask that is capable for use with both a child and an adult. Specifically, this mask resembles a conventional mask but has indicia printed on its face to indicate by axis of readability which way it is to be positioned when used on either an adult or a child.

Hence, this single mask can be used on both an adult and a child when positioned properly and therefore, eliminates the need for a special child-size mask. Accordingly, less time is wasted in locating a child-size mask and ultimately administering oxygen and/or resuscitation to a child. Also, the additional storage space needed for storing these child-size masks is eliminated.

BRIEF DESCRIPTION OF THE DRAWINGS

These and other objects and advantages of the invention will become more apparent and more readily appreciated from the following detailed description of the presently preferred exemplary embodiments of the invention taken in conjunction with the accompanying drawings, of which.

DESCRIPTION OF THE PREFERRED EMBODIMENTS

Figure 1:
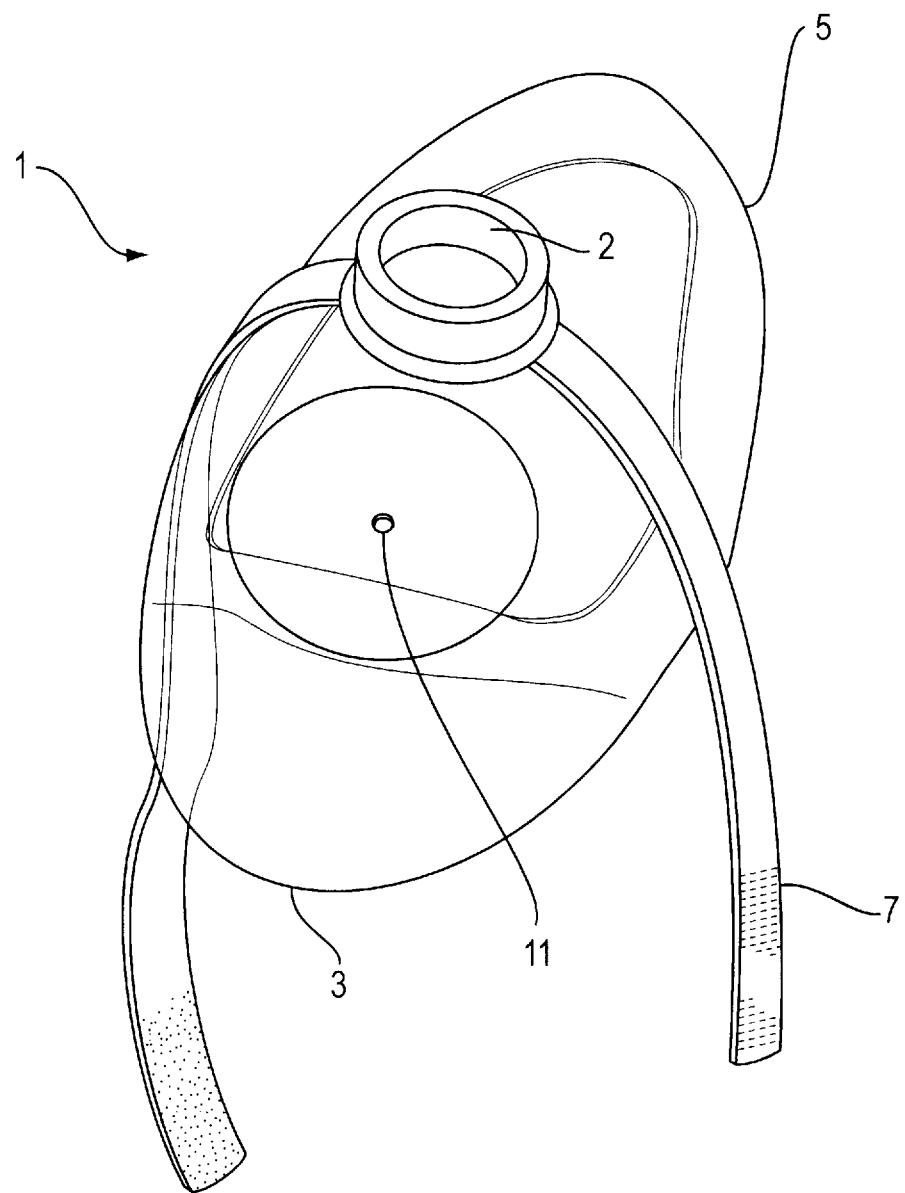
FIG. 1 illustrates a perspective view of a conventional inhalator and/or resuscitator mask.
Figure 2:
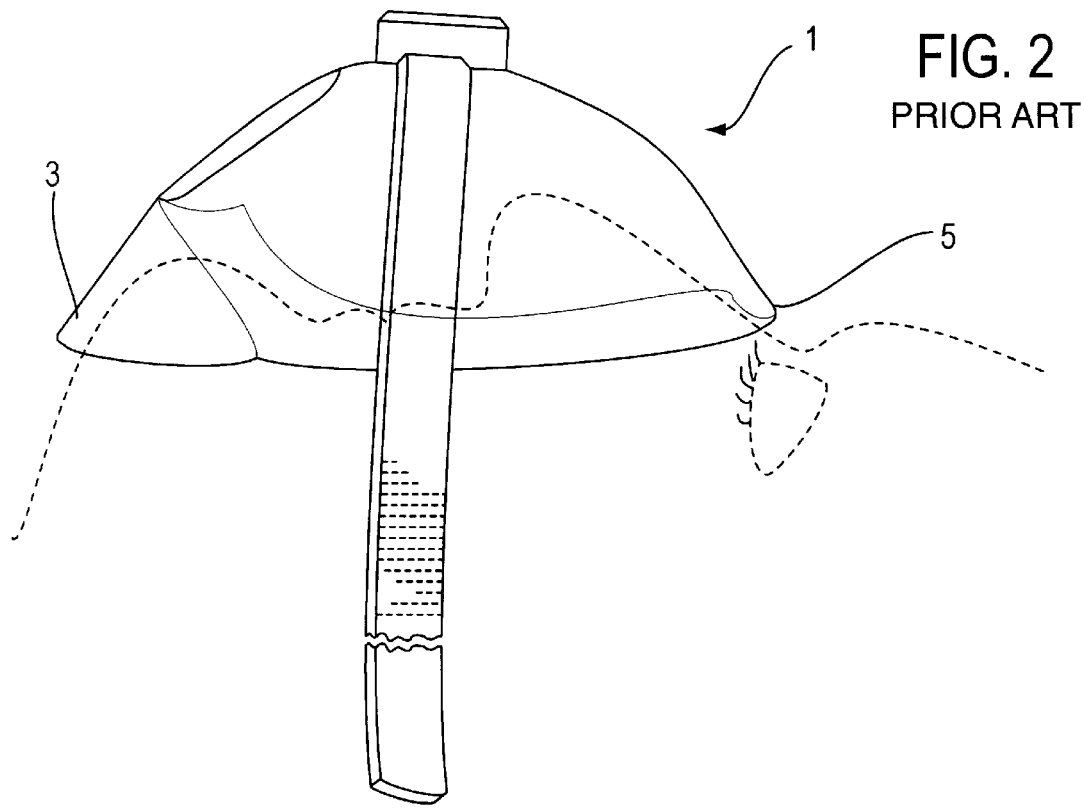
FIG. 2 illustrates the application of a conventional mask to an adult.
Figure 3:
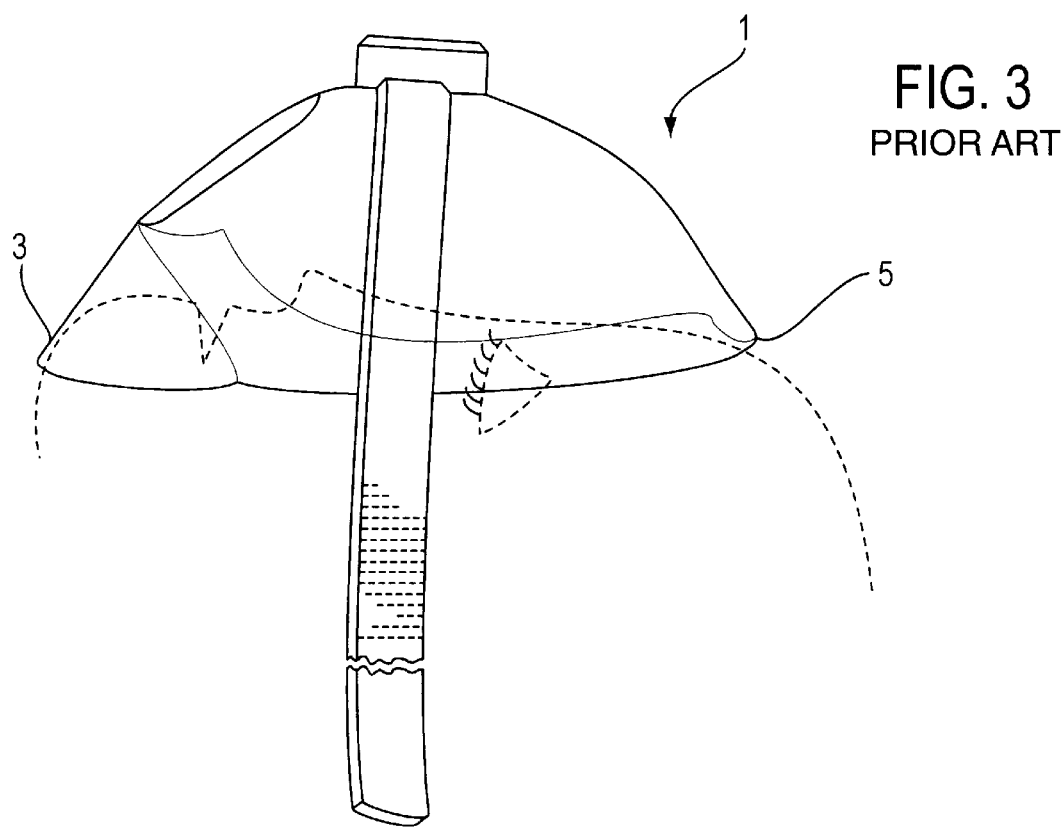
FIG. 3 illustrates the application of a conventional mask to a child.
Figure 4:
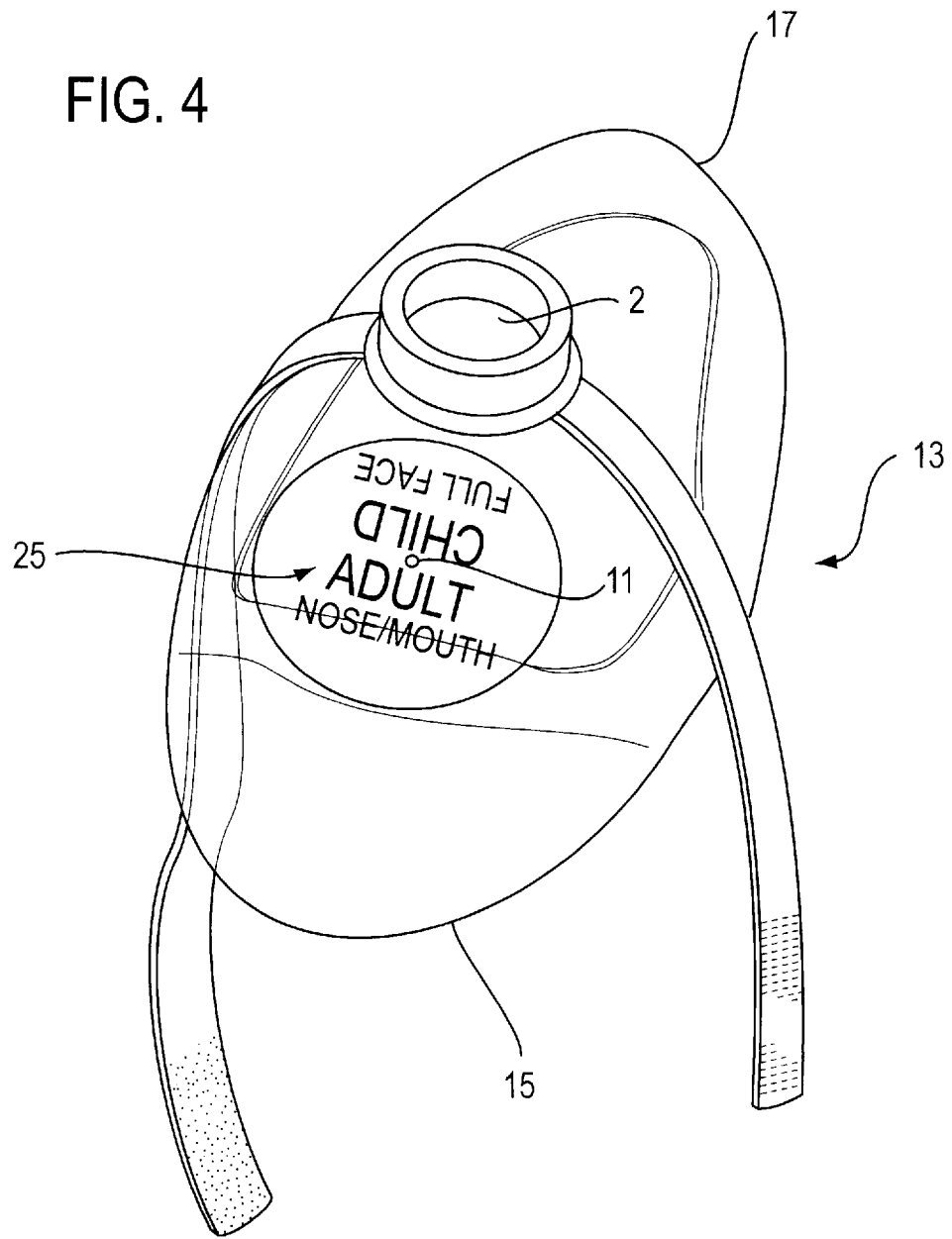
FIG. 4 illustrates perspective view of an embodiment of the mask of the present invention.
Figure 5:
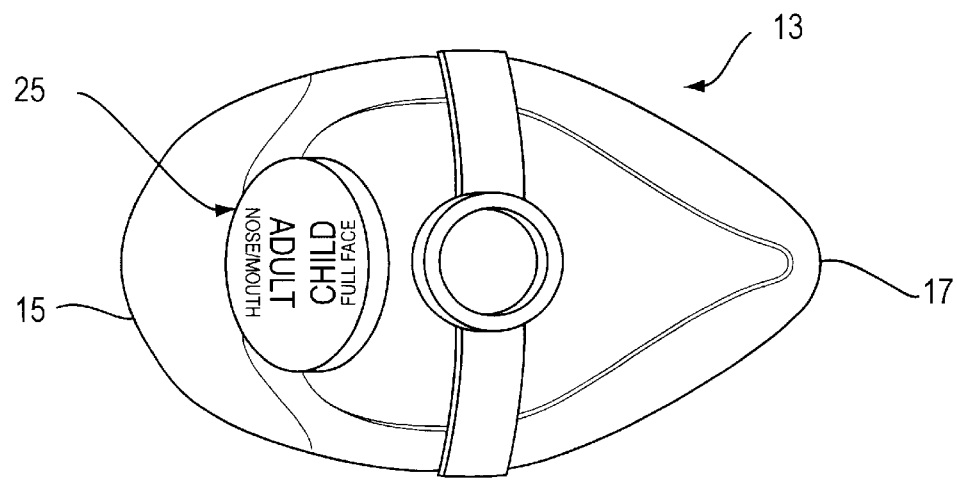
FIG. 5 illustrates a top view of the embodiment shown in FIG. 4.

FIG. 4 illustrates a perspective view of an embodiment of the inhalator and/or resuscitator mask of the present invention. A top view of the embodiment shown in FIG. 4 is presented in FIG. 5. Particularly, this mask 13 resembles the conventional mask in that it is constructed of a pliable material such as plastic, rubber, or the like. The mask 13 has a wide end 15 and a narrow end 17, and can include straps 21 for securing the mask 13 to a person's head. Moreover, the mask 13 can include a hole 11 into which a tube (not shown) is inserted to provide oxygen to the mask 13. The mask may include a hole 2 to which is applied positive pressure to resuscitate a victim, or holes, both of which allow inhalation and exhalation as free breathing masks.

Figure 6:
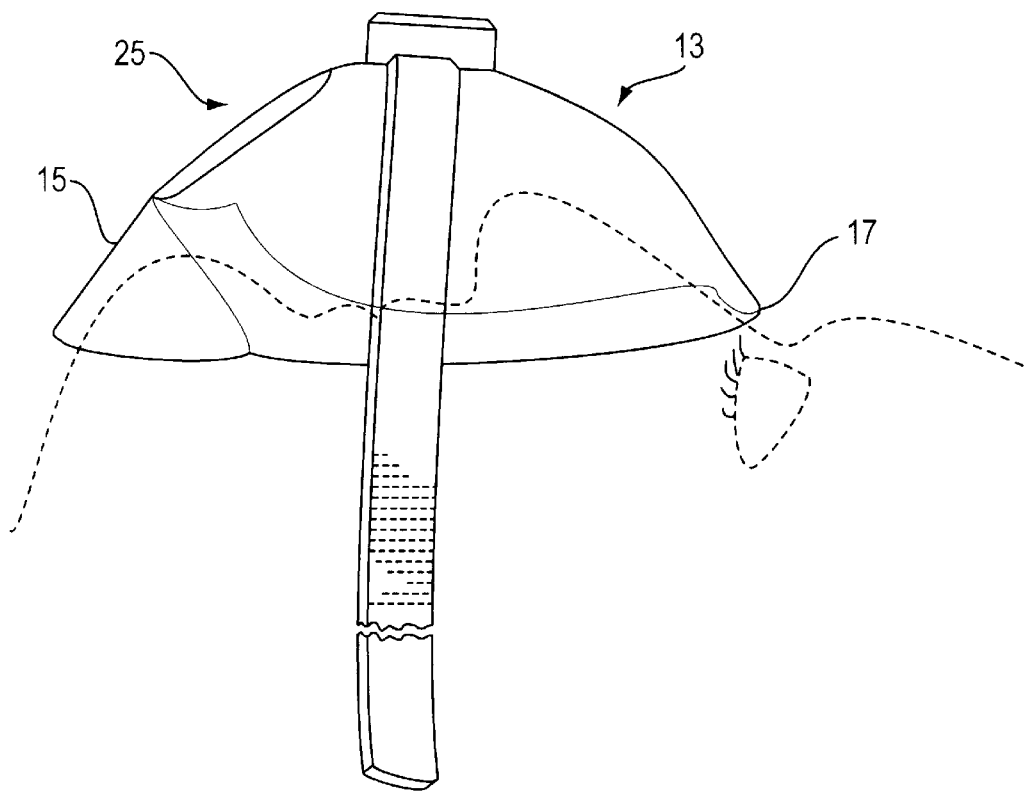
FIG. 6 illustrates the application of the mask of the present invention to an adult.

The mask 13 of the present invention also includes indicia 25 on its face. This indicia 25 indicates the manner in which the mask is to be positioned when used on a child or an adult. In particular, the word "ADULT" should be read right side up in a direction from the chin upward when the mask is used on an adult or a person having an adult-size face. Therefore, as shown in FIG. 6, the wide end 15 of the mask 13 which is below the "ADULT" indicia should be placed proximate to the adult's chin, while the narrow end 17 of the mask 13 should be placed over the bridge of the adult's nose, thus to allow an airtight seal to form between the adult's face and the mask.

Figure 7:
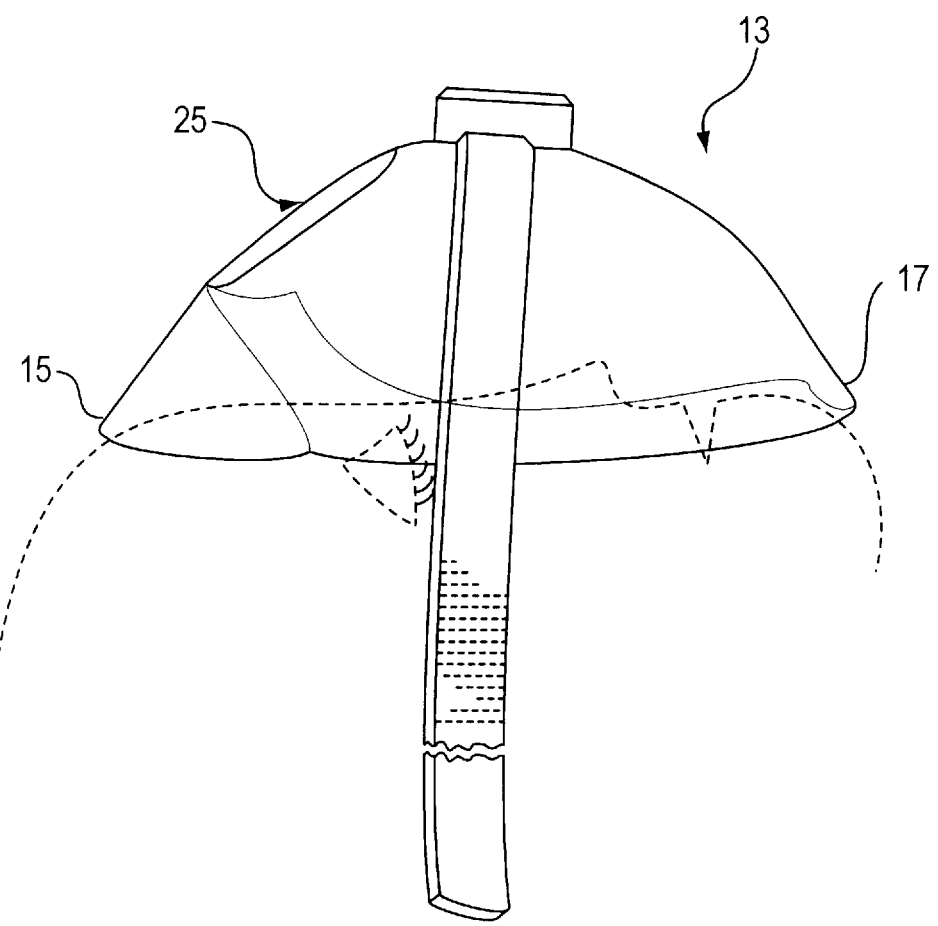
FIG. 7 illustrates the application of the mask of the present invention to a child.

Conversely, the indicia "CHILD" indicates that the mask 13 is to be turned upside down when the mask is to be applied to the face of a child. In particular, the word "CHILD" should read right side up in a direction from the chin upward when the mask is used on a child or a person having a child size face. Hence, when the mask is applied to a child's face or a person having a child-size face, as shown in FIG. 7, the narrow end 17 of the mask 13 should be positioned proximate to the child's chin while the larger end 15 of the mask 13 should be positioned over the upper portion of the child's face. Thus, the mask 13 will cover substantially all of the child's face and allow an airtight or substantially airtight seal to form between the child's face and the mask. Again, it is clear that the invention provides a bi-orientatable mask capable of delivering a gas to a victim or patient. The mask comprises a mask body of flexible material in which at least two sets of indicia are provided on said mask body, said sets of indicia each provide both an axis of orientation and a size or shape designator, said indicia are arranged such that when said mask is correctly oriented on said patient or victim, the size or shape designator of only one of said sets of indicia is oriented such that the size or shape of said patient or victim is accurately indicated.

The sets of indicia each comprise alphanumeric characters providing an inherent axis of orientation, and said alphanumeric characters form a word or pattern which includes said size or shape designator. Each of said size or shape designators is a word or words indicating the size or shape of the patient or victim, and wherein when said mask is correctly oriented on said patient or victim, said word or words are oriented right side up and correctly identify the size or shape of said patient or victim.

A first of said size or shape designators indicates that a first end of said mask is to be positioned proximate the chin of a patient or victim having an adult-size face, and a second of said size or shape designators indicates that a second end of said mask is to be positioned proximate the chin of a patient or victim having a child-size face when the mask is applied.

The indicia 25 can be any symbol, letter, or the like which would indicate to a person using the mask how to position the mask properly for use with an adult or a child. In an embodiment shown in FIG. 5, said first and second sets of indicia consist of English letters. Said first set of indicia includes the word "ADULT" and said second set of indicia includes the word "CHILD", said first and seconds sets of indicia are oriented on respective axes which are approximately 180 degrees apart. Also, the indicia 25 can be formed as part of the mask 13, or be printed on a label or the like which is attached to the mask 13. In an embodiment, said first and second sets of indicia each are integral with said mask. In another embodiment, a member on which said first and second sets of indicia are disposed is attached to said mask. Of course, the indicia 25 can be in any language, and can be colored or highlighted for easy reading. Also, the indicia 25 can be a fluorescent or glow in the dark luminescent type indicia which can be viewed easily during evening hours or adverse weather conditions when, for example, automobile accidents, which often result in oxygen or/and resuscitation being administered to the victims, frequently occur. The present invention further provides a method for using a bi-orientable mask for supplying oxygen or resuscitation to a person having an adult-size face or a person having a child-size face, comprising the steps of:

determining the size of the face of the person with which the mask is to be used, and positioning said mask on the face of the person in one of two orientations, said orientation being selected such that an indicia on said mask which properly indicates the size of the face of said person is right side up when said mask is in place. The positioning step includes the step of positioning a first end of said mask proximate to the chin of a person having an adult-size face; and positioning a second end of said mask proximate to the chin of a person having a child-size face, when the mask is applied.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

What is claimed is:

1. A bi-orientable mask capable of delivering a gas to a victim or patient, comprising:

a mask body of flexible material;

at least two sets of indicia provided on said mask body;

said sets of indicia each providing both an axis of orientation and a patient or victim size or shape designator, said indicia being arranged such that when said mask is correctly oriented on a patient or victim, the size or shape designator of only one of said sets of indicia is oriented such that the size or shape of a patient or victim is accurately indicated.

2. A mask as claimed in claim 1, wherein said sets of indicia each comprise alphanumeric characters providing an inherent axis of orientation, and said alphanumeric characters form a word or pattern which includes said size or shape designator.

3. A mask as claimed in claim 2, wherein each of said size or shape designators is a word or words indicating the size or shape of a patient or victim, and wherein when said mask is correctly oriented on a patient or victim, said word or words are oriented right side up and correctly identify the size or shape of a patient or victim.

4. A mask as claimed in claim 2, wherein a first of said size or shape designators indicates that a first end of said mask is to be positioned proximate chin of a patient or victim having an adult-size face, and a second of said size or shape designators indicates that a second end of said mask is to be positioned proximate a chin of a patient or victim having a child-size face when the mask is applied.

5. A mask as claimed in claim 1, wherein said first and second sets of indicia consist of English letters.

6. A mask as claimed in claim 1, wherein said first set of indicia includes the word "ADULT" and said second set of indicia includes the word "CHILD", said first and seconds sets of indicia being oriented on respective axes which are approximately 180 degrees apart.

7. A mask as claimed in claim 1, wherein said first and second sets of indicia each are integral with said mask.

8. A mask as claimed in claim 1, further comprising a member on which said first and second sets of indicia are disposed, said member being attached to said mask.

9. A method for using a bi-orientable mask for supplying oxygen or resuscitation to a person having an adult-size face or a person having a child-size face, comprising the steps of:

providing a flexible mask body having top and bottom ends and at least two sets of indicia thereon, the sets of indicia providing (1) an axis of orientation, said sets of indicia being seperated by approximately 180 degrees, and (2) a designator indicative of the size or shape of a patient or victim;

determining the size or shape of the face of a person with which said mask is to be used, and positioning said mask on the face of a person in a first one of two orientations, the first one of said two orientations being selected such that one of the two sets of indicia on said mask properly indicates the size of the face of a person when said mask is in place, or positioning said mask on the face of a person in a second one of said two orientations with respect to the first one of said two orientations by reversing said top and bottom ends of said mask with respect to a person's face so that the other one of the sets of indicia on said mask properly indicates the size of the face of the person when said mask is in place.

10. A method as claimed in claim 9, wherein:

said positioning step includes the step of positioning said top end of said mask proximate to a chin of a person having an child size face; and positioning said bottom end of said mask proximate to the chin of a person having a adult size face, when the mask is applied.

11. A bi-orientable mask capable of delivering a gas to a victim or a patient, comprising:

a mask body of flexible material and having top and bottom ends;

at least two sets of indicia provided on said mask body;

said sets of indicia each providing (1) an axis of orientation and (2) a designator indicative of the size or shape of a patient or victim, said sets of indicia being arranged such that when said mask is correctly oriented on a patient or victim, the size or shape designator of only one of said sets of indicia is oriented such that the size or shape of a patient or victim is accurately indicated;

wherein the axes of orientation respectively provided by first and second of said sets of indicia are angularly separated by approximately 180°.

12. A mask as claimed in claim 11, wherein a second of said two orientations is achieved by reversing said top and bottom ends of said mask with respect to the face of a patient or victim.

\* \* \* \* \*